United States Patent
Fuerderer

(10) Patent No.: US 9,861,401 B2
(45) Date of Patent: Jan. 9, 2018

(54) DEVICE FOR STRAIGHTENING AND STABILIZING THE VERTEBRAL COLUMN

(71) Applicant: DePuy Synthes Products, Inc., Raynham, MA (US)

(72) Inventor: Sebastian Fuerderer, Mainz (DE)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/044,367

(22) Filed: Feb. 16, 2016

(65) Prior Publication Data

US 2016/0157898 A1 Jun. 9, 2016

Related U.S. Application Data

(60) Continuation of application No. 13/924,881, filed on Jun. 24, 2013, now Pat. No. 9,295,502, which is a
(Continued)

(30) Foreign Application Priority Data

Nov. 3, 2001 (DE) .................................. 101 54 163

(51) Int. Cl.
*A61F 2/44* (2006.01)
*A61B 17/70* (2006.01)
(Continued)

(52) U.S. Cl.
CPC ...... *A61B 17/7097* (2013.01); *A61B 17/8858* (2013.01); *A61M 25/10* (2013.01);
(Continued)

(58) Field of Classification Search
CPC ............ A61F 2/447; A61F 2002/30537; A61F 2002/30545; A61F 2002/3055;
(Continued)

(56) References Cited

U.S. PATENT DOCUMENTS

| 2,381,050 A | 8/1945 | Hardinge |
| 3,701,703 A | 10/1972 | Zimmer et al. |

(Continued)

FOREIGN PATENT DOCUMENTS

| DE | 195 08 805 A1 | 11/1996 |
| EP | 0 493 789 B1 | 3/1997 |
| JP | 11-076246 A | 3/1999 |
| WO | 97/16219 A1 | 5/1997 |
| WO | 98/38918 A1 | 9/1998 |

(Continued)

OTHER PUBLICATIONS

Cotten, Anne., MD., et al. "Percutaneous Vertebroplasty for Osteolytic Metastases and Myeloma: Effects of the Percentage of Lesion Filling and the Leakage of Methyl Methacrylate at Clinical Follow-up"., Radiology 1996; 200:525-530.

(Continued)

*Primary Examiner* — Eduardo C Robert
*Assistant Examiner* — Michelle C Eckman
(74) *Attorney, Agent, or Firm* — Nutter McClennen & Fish LLP

(57) ABSTRACT

A device for straightening and stabilizing the vertebral column, particularly for stabilizing broken vertebrae, includes a supporting implant which is plastically expandable by internal pressure. The supporting implant can be placed into the interior of a vertebral body which has been fractured under compression or between adjacent vertebral bodies. A pressure balloon to which pressure fluid can be admitted may be arranged in the interior of the supporting implant for producing the internal pressure.

15 Claims, 2 Drawing Sheets

Related U.S. Application Data continuation of application No. 12/268,215, filed on Nov. 10, 2008, now Pat. No. 8,491,591, which is a division of application No. 10/286,458, filed on Nov. 1, 2002, now abandoned.

(51) Int. Cl.
   *A61B 17/88* (2006.01)
   *A61M 25/10* (2013.01)
   *A61B 17/00* (2006.01)
   *A61B 17/02* (2006.01)

(52) U.S. Cl.
   CPC ............ *A61B 2017/00539* (2013.01); *A61B 2017/00557* (2013.01); *A61B 2017/0256* (2013.01); *A61M 2025/1004* (2013.01); *A61M 2210/02* (2013.01)

(58) Field of Classification Search
   CPC .. A61F 2002/30551; A61F 2002/30556; A61F 2/44; A61F 2/4611
   USPC .......................................... 606/99, 105, 86 R
   See application file for complete search history.

(56) References Cited

U.S. PATENT DOCUMENTS

| | | |
|---|---|---|
| 4,055,029 A | 10/1977 | Kalbow |
| 4,820,305 A | 4/1989 | Harms et al. |
| 4,820,349 A | 4/1989 | Saab |
| 4,969,888 A | 11/1990 | Scholten et al. |
| 4,976,725 A | 12/1990 | Chin et al. |
| 5,041,114 A | 8/1991 | Chapman et al. |
| 5,059,193 A | 10/1991 | Kuslich |
| 5,108,404 A | 4/1992 | Scholten et al. |
| 5,192,326 A | 3/1993 | Bao et al. |
| 5,342,298 A | 8/1994 | Michaels et al. |
| 5,390,683 A | 2/1995 | Pisharodi |
| 5,443,496 A | 8/1995 | Schwartz et al. |
| 5,549,679 A | 8/1996 | Kuslich |
| 5,599,301 A | 2/1997 | Jacobs et al. |
| 5,601,593 A | 2/1997 | Freitag |
| 5,674,277 A | 10/1997 | Freitag |
| 5,693,100 A | 12/1997 | Pisharodi |
| 5,707,390 A | 1/1998 | Bonutti |
| 5,759,191 A | 6/1998 | Barbere |
| 5,792,300 A | 8/1998 | Inderbitzen et al. |
| 5,827,289 A | 10/1998 | Reiley et al. |
| 5,893,850 A | 4/1999 | Cachia |
| 5,972,015 A | 10/1999 | Scribner et al. |
| 6,019,793 A * | 2/2000 | Perren ............. A61F 2/442 623/17.16 |
| 6,096,038 A | 8/2000 | Michelson |
| 6,127,597 A | 10/2000 | Beyar et al. |
| 6,179,856 B1 | 1/2001 | Barbere |
| 6,183,503 B1 | 2/2001 | Hart et al. |
| 6,200,347 B1 * | 3/2001 | Anderson ............ A61F 2/28 623/11.11 |
| 6,235,043 B1 | 5/2001 | Reiley et al. |
| 6,241,734 B1 | 6/2001 | Scribner et al. |
| 6,245,107 B1 | 6/2001 | Ferree |
| 6,248,110 B1 | 6/2001 | Reiley et al. |
| 6,306,177 B1 | 10/2001 | Felt et al. |
| 6,395,032 B1 | 5/2002 | Gauchet |
| 6,440,138 B1 | 8/2002 | Reiley et al. |
| 6,478,800 B1 | 11/2002 | Fraser et al. |
| 6,558,390 B2 | 5/2003 | Cragg |
| 6,582,467 B1 * | 6/2003 | Teitelbaum ........ A61B 17/1615 623/17.11 |
| 6,613,054 B2 | 9/2003 | Scribner et al. |
| 6,620,162 B2 | 9/2003 | Kuslich et al. |
| 6,632,235 B2 | 10/2003 | Weikel et al. |
| 6,663,647 B2 | 12/2003 | Reiley et al. |
| 6,679,886 B2 | 1/2004 | Weikel et al. |
| 6,706,069 B2 | 3/2004 | Berger |
| 6,716,216 B1 | 4/2004 | Boucher et al. |
| 6,719,761 B1 | 4/2004 | Reiley et al. |
| 6,726,691 B2 | 4/2004 | Osorio et al. |
| 6,733,532 B1 | 5/2004 | Gauchet et al. |
| 6,740,093 B2 | 5/2004 | Hochschuler et al. |
| 6,863,672 B2 | 3/2005 | Reiley et al. |
| 6,899,719 B2 | 5/2005 | Reiley et al. |
| 6,981,981 B2 | 1/2006 | Reiley et al. |
| 7,025,771 B2 | 4/2006 | Kuslich et al. |
| 7,044,954 B2 | 5/2006 | Reiley et al. |
| 7,097,648 B1 | 8/2006 | Globerman et al. |
| 7,108,714 B1 | 9/2006 | Becker |
| 7,112,216 B2 | 9/2006 | Gregorich |
| 7,153,307 B2 | 12/2006 | Scribner et al. |
| 7,166,121 B2 | 1/2007 | Reiley et al. |
| 7,226,481 B2 | 6/2007 | Kuslich |
| 7,241,303 B2 | 7/2007 | Reiss et al. |
| 7,261,720 B2 | 8/2007 | Stevens et al. |
| 8,491,591 B2 | 7/2013 | Fuerderer |
| 9,295,502 B2 | 3/2016 | Fuerderer |
| 2001/0012946 A1 | 8/2001 | MacKenzie et al. |
| 2002/0026195 A1 | 2/2002 | Layne et al. |
| 2002/0058947 A1 | 5/2002 | Hochschuler et al. |
| 2002/0068974 A1 | 6/2002 | Kuslich et al. |
| 2002/0156529 A1 | 10/2002 | Li et al. |
| 2003/0050702 A1 | 3/2003 | Berger |
| 2003/0088249 A1 | 5/2003 | Furderer |
| 2003/0130664 A1 | 7/2003 | Boucher et al. |
| 2003/0220649 A1 | 11/2003 | Bao et al. |
| 2004/0010315 A1 * | 1/2004 | Song ................. A61F 2/44 623/17.16 |
| 2004/0073308 A1 | 4/2004 | Kuslich et al. |
| 2004/0097930 A1 | 5/2004 | Justis et al. |
| 2004/0102774 A1 | 5/2004 | Trieu |
| 2004/0143330 A1 | 7/2004 | Sazy |
| 2004/0167625 A1 | 8/2004 | Beyar et al. |
| 2004/0210297 A1 | 10/2004 | Lin et al. |
| 2004/0215343 A1 | 10/2004 | Hochschuler et al. |
| 2004/0215344 A1 | 10/2004 | Hochschuler et al. |
| 2004/0220615 A1 | 11/2004 | Lin et al. |
| 2005/0070911 A1 | 3/2005 | Carrison et al. |
| 2005/0143827 A1 | 6/2005 | Globerman et al. |
| 2005/0234498 A1 | 10/2005 | Gronemeyer et al. |
| 2006/0079905 A1 | 4/2006 | Beyar et al. |
| 2006/0100706 A1 | 5/2006 | Shadduck et al. |
| 2006/0190083 A1 | 8/2006 | Arnin et al. |
| 2006/0210605 A1 | 9/2006 | Chang et al. |
| 2006/0217795 A1 | 9/2006 | Besselink et al. |
| 2006/0271061 A1 | 11/2006 | Beyar et al. |
| 2006/0293750 A1 | 12/2006 | Sherman et al. |
| 2007/0055266 A1 | 3/2007 | Osorio et al. |
| 2007/0055267 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio et al. |
| 2007/0219634 A1 * | 9/2007 | Greenhalgh ........ A61F 2/446 623/17.16 |
| 2007/0282443 A1 | 12/2007 | Globerman et al. |
| 2009/0069850 A1 | 3/2009 | Fuerderer |
| 2013/0310877 A1 | 11/2013 | Fuerderer |

FOREIGN PATENT DOCUMENTS

| | | |
|---|---|---|
| WO | 98/56301 A1 | 12/1998 |
| WO | 99/24223 A1 | 5/1999 |
| WO | 00/44319 A1 | 8/2000 |
| WO | 01/76514 A2 | 10/2001 |
| WO | 02/43628 A1 | 6/2002 |
| WO | 02/076678 A1 | 10/2002 |
| WO | 03/007853 A1 | 1/2003 |
| WO | 2005/048856 A1 | 6/2005 |

OTHER PUBLICATIONS

Cotten, Anne, et al., "Preoperative Percutaneous Injection of Methyl Methacrylate and N-Butyl Cyanoacrylate in Vertebral Hemangiomas"; AJNR 17:137-142 (1996).

(56) References Cited

OTHER PUBLICATIONS

European Search Report for Application No. 02024098.2, dated May 15, 2003 with an English Translations of the pertinent portions (101896-1387) (4 pages).
Gangi, Afshin, et al., "Percutaneous Vertebroplasty Guided by a Combination of CT and Fluoroscopy", AJNR 15:83-86, Jan. 1994.
Japanese Office Action for Application No. 2002-346496, dated Nov. 25, 2008. Includes Japanese Search (18 pages).
Jensen, Mary E., et al., "Percutaneous Polymethylmethacrylate Vertebroplasty in the Treatment of Osteoporotic Vertebral Body CompressionFractures: Technical Aspects", AJNR: Nov. 18, 1997.
Maciunas, Robert J., MD., "Endovascular Neurological Intervention"; American Association of Neurological Surgeons; 153-158.

* cited by examiner

DEVICE FOR STRAIGHTENING AND STABILIZING THE VERTEBRAL COLUMN

CROSS-REFERENCE TO RELATED APPLICATIONS

This application is a continuation of U.S. application Ser. No. 13/924,881 filed on Jun. 24, 2013, which is a continuation of U.S. application Ser. No. 12/268,215 filed on Nov. 10, 2008, which is a divisional of U.S. application Ser. No. 10/286,458 filed on Nov. 1, 2002, which claims priority to German Patent Application No. DE 101 54 163.5 filed Nov. 3, 2001, the entire contents of each of these applications is incorporated herein by reference.

BACKGROUND OF THE INVENTION

1. Field of the Invention

The present invention relates to a device for straightening and stabilizing the vertebral column, particularly for stabilizing broken vertebrae.

2. Description of the Related Art

Devices for straightening and stabilizing broken vertebrae are known to be used. These devices include a catheter which can be inserted into the interior of the vertebra through a duct drilled into the pedicle of the broken vertebra. A pressure line pushed through the catheter into the interior of the vertebra has at the end thereof an expandable pressure balloon which makes it possible to expand once again and return into its original shape a vertebra which has been compressed and possibly broken. The balloon which has subsequently been decompressed and pulled out together with the pressure line leaves a hollow space into which a bone filler material can be introduced through the catheter.

SUMMARY OF THE INVENTION

It is the primary object of the present invention to provide a novel device for stabilizing the vertebral column, particularly for straightening and stabilizing broken vertebrae, which makes it possible to achieve a higher degree of stabilization more quickly than by using the known devices, wherein the required operation is simpler.

In accordance with the present invention, the device for straightening and stabilizing the vertebral column is characterized by a supporting implant which is plastically expandable by internal pressure.

Such a supporting implant, which is preferably provided for being arranged in the interior of a vertebral body fractured under compression or also, for example, after an intervertebral disc resection for arrangement between adjacent vertebral bodies, can be easily moved to the implantation location because of its small dimensions. After the expansion has been effected, a preliminary stabilization is ensured immediately because the supporting implant maintains its final shape obtained during the plastic expansion. A filler material which is initially present in liquid form can be introduced under slight pressure into the created hollow space and can harden in the hollow space. Because of the action of the supporting implant, it is not necessary to wait until the filler material has hardened completely.

While mechanical tools for producing the internal pressure are conceivable, a preferred embodiment of the invention provides for a device which produces the internal pressure by means of a pressure fluid.

The pressure fluid can be introduced directly into the supporting implant, which requires that the supporting implant and the supply connections are pressure tight. However, in accordance with a preferred embodiment, a pressure balloon is provided which is arranged in the interior of the supporting implant and into which the pressure fluid can be introduced.

The expandable supporting implant may include a weakened wall, or a wall which is perforated in the manner of expanded metal and/or folded in the manner of a bellows.

This type of supporting implant can be expanded with relatively low internal pressure, wherein the stability of the expanded implant is reduced by the weakened or folded portions, however, the implant can still carry out a sufficient supporting function.

The wall of the expandable supporting implant may have weak portions and/or folds arranged in such a way that the supporting implant expands into a desired shape. For example, if such a supporting implant is arranged between adjacent vertebrae, the desired shape is approximately that of a parallelepiped.

In accordance with a preferred embodiment of the invention, the expandable supporting implant has an oblong shape so that it is suitable for being arranged at the implantation location by means of a catheter or a guide sleeve. In particular, the expandable supporting implant, and possibly the pressure balloon, may be placed in the manner of a stocking on a pressure line which can be introduced through the guide sleeve, wherein the pressure balloon is arranged between the supporting implant and the pressure line and, in the non-expanded state, forms a hose-type sleeve which surrounds the pressure line and which is connected at its ends in a pressure-tight manner by being placed around the circumference of the pressure line.

The pressure fluid is preferably not compressible, and a device for measuring the supplied amount of pressure fluid is provided. This makes it possible to control the degree of expansion through the supplied quantity.

In accordance with another advantageous embodiment of the invention, a monitoring device is provided which monitors changes over time of the fluid pressure and the supplied fluid quantity so that the pressure application can be interrupted when predetermined relative values of these changes are exceeded. Such a monitoring device prevents fluid which is under high pressure from being released into the body when the supporting implant is destroyed, for example, as a result of a material defect.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE INVENTION

Figure 1:
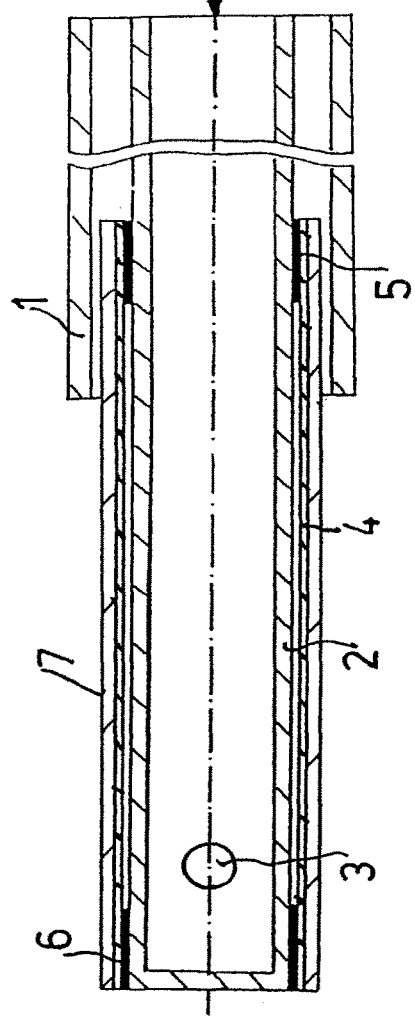
FIG. 1 is a schematic sectional view of a device according to the invention with a supporting implant placed on a pressure line.
Figure 1:
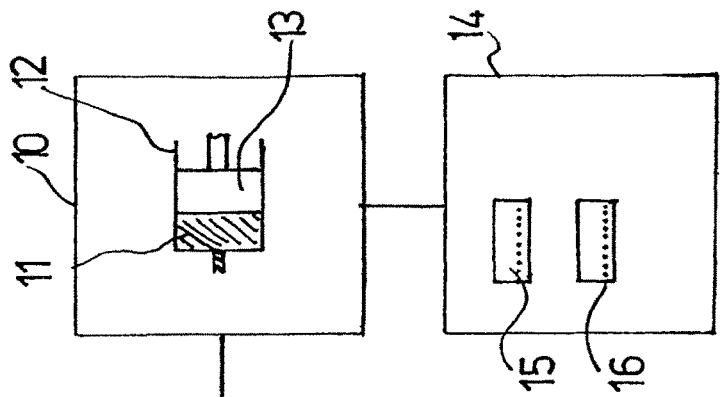
Figure 5:
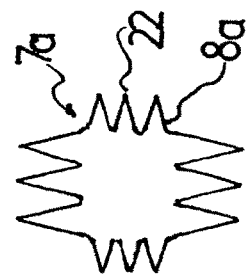
FIG. 5 is an illustration of another embodiment of the supporting implant which can be used in a device of the invention.

FIG. 1 of the drawing shows a guide sleeve 1 and a pressure line 2 extending through the guide sleeve 1, wherein the pressure line 2 is provided with an opening 3 for releasing a pressure fluid.

An elastic hose-type sheath 4 is placed in the manner of a stocking and flush at the ends thereof on the circular cylindrical pressure line 2. The sheath 4 is glued in a pressure-tight manner at its ends to the circumference of the pressure line 2 at 5 and 6. Instead of providing a glued connection, it would also be possible to press the elastic sheath 4 at the ends thereof by means of rings against the pressure line.

Figure 2:
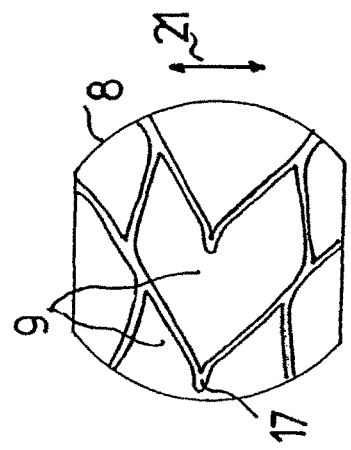
FIG. 2 is an illustration of a detail of the supporting implant of FIG. 1.

A hollow-cylindrical supporting implant 7 is placed around the elastic sheath 4. As can be seen in FIG. 2, the cylindrical wall 8 of the implant 7 is a mesh-like material with openings 9, wherein wires of the mesh extend at an acute angle relative to each other. The wall 8 can be tangentially expanded in the manner of expanded metal in the direction of double arrow 21, so that the supporting implant 7 is radially expanded.

At its end opposite the sheath 4 or the supporting implant 7, the pressure line 2 is in connection with a schematically illustrated device 10 for supplying an incompressible pressure fluid 11, wherein this device 10 includes a pressure cylinder 12 and a piston 13. The piston 13 may be movable manually, preferably by means of a screw-type pressure gauge, or by means of a motor drive.

Reference numeral 14 denotes a schematically illustrated control and monitoring device which includes a pressure indicator 16 and a display 17 for the supplied quantity of pressure fluid.

Figure 3:
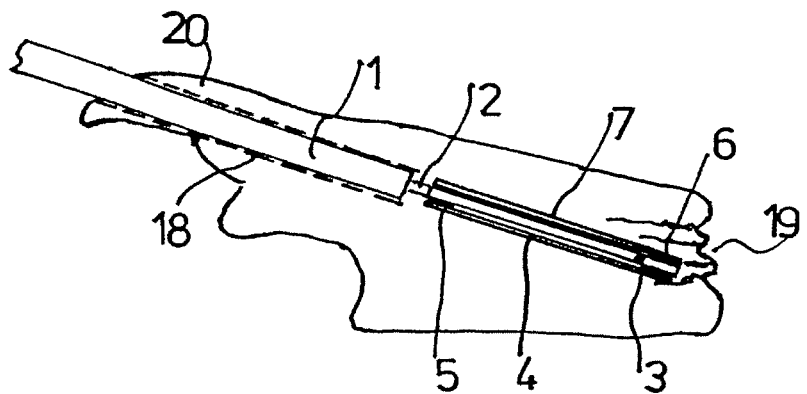
FIG. 3 is an illustration, on a smaller scale, showing the device of FIG. 1 inserted into a broken and compressed vertebral body.

The manner of operation of the device is shown in FIGS. 1 and 2 and shall now be explained in connection with FIGS. 3 and 4.

For stabilizing a broken vertebra, initially a duct 18 is drilled through the pedicle 20, wherein a catheter and a drilling tool extending through the catheter can be used for this purpose. As shown in FIGS. 3 and 4, the guide sleeve 1 is now placed in the duct 18 and the pressure fluid 2 with the supporting implant 7 can be forwardly pushed into the interior of the compressed vertebra which has compression folds at 19.

The incompressible pressure fluid 11 is pressed by means of the device 10 into the pressure line 2, the pressure fluid 11 emerges from the opening 3 and the elastic sheath 4 is expanded into a balloon. The expanding sheath or balloon 4 expands the supporting implant 7, as illustrated in FIG. 4, wherein the wall 8 of the supporting implant 7 is plastically deformed in the direction of arrow 21 shown in FIG. 2 and the acute angles between the mesh wires at 17 are widened.

The quantity of supplied pressure fluid during the expansion can be read at the display 17 of the control and monitoring device 14 and, thus, the extent of the achieved expansion can be determined. The expansion or supply of pressure fluid is stopped when a predetermined value of the supplied pressure fluid quantity has been reached.

The control and monitoring device 14 further ensures that the application of pressure is stopped immediately if the balloon 4 ruptures during the expansion, for example, due to a material defect, and pressure fluid is released from the vertebra; this is the case when the supplied pressure fluid quantity increases significantly over time, while the pressure stays constant or increases only slightly.

After the required expansion has been achieved, the pressure fluid is withdrawn through the opening 3 which is located near the lowest point of the balloon 4. The pressure line 2 with the empty pressure balloon or the empty sheath 4 can now be pulled back through the guide sleeve 1.

Figure 4:
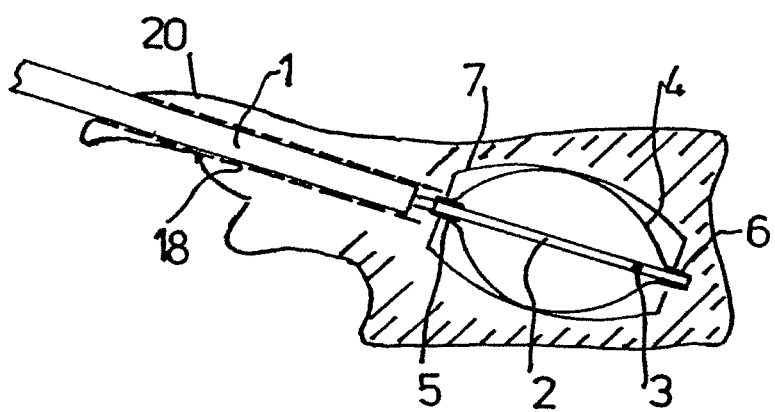
FIG. 4 shows the vertebral body of FIG. 3 which has been expanded by means of the device of FIG. 1.

The plastically deformed supporting implant 7 maintains its shape and supports the vertebra in such a way that it maintains the shape shown in FIG. 4 and the damage shown at 19 can heal. A filler material is introduced into the interior of the supporting implant.

FIG. 2 is a cross-sectional view of another embodiment of a supporting implant 7a according to the invention. The supporting implant 7a has in its wall 8a folds 22, wherein the folds on opposite sides have different lengths, so that the expanded implant has a rectangular shape in cross-section.

In the embodiment described above, a salt solution containing an x-ray contrast agent is used as the pressure fluid.

Of course, two of the above-described supporting implants can be and are usually inserted into a broken vertebra, wherein ducts are drilled in both pedicles for inserting a catheter.

While specific embodiments of the invention have been shown and described in detail to illustrate the inventive principles, it will be understood that the invention may be embodied otherwise without departing from such principles.

I claim:

1. A spinal implant, comprising:
   opposed superior and inferior sidewalls; and
   opposed lateral sidewalls,
   wherein the implant has a non-expanded state and an expanded state, the lateral sidewalls being expanded in height in the expanded state as compared to the non-expanded state and the superior and inferior sidewalls being expanded in width in the expanded state as compared with the non-expanded state,
   wherein the implant in the non-expanded state has a substantially rectangular transverse cross-section defined by the superior and inferior sidewalls and the lateral sidewalls, the superior and inferior sidewalls having a plurality of folds that each define a two-sided section of a triangle;
   wherein the implant in the expanded state defines a hollow cavity configured to be filled with a filler material; and
   wherein the implant is positionable in a disc space between adjacent vertebral bodies and configured to be expanded within the disc space to support the adjacent vertebral bodies.

2. The spinal implant of claim 1, wherein the implant is expandable by internal pressure.

3. The spinal implant of claim 2, further comprising a mechanical tool for producing the internal pressure.

4. The spinal implant of claim 1, wherein the implant is configured to maintain its shape in the expanded state.

5. The spinal implant of claim 1, wherein the opposed superior and inferior sidewalls include perforations.

6. The spinal implant of claim 1, wherein the opposed lateral sidewalls are folded.

7. The spinal implant of claim 1, wherein the opposed lateral sidewalls include perforations.

8. The spinal implant of claim 1, wherein the implant has an approximately parallelepiped shape.

9. The spinal implant of claim 1, wherein the lateral sidewalls of the implant in the non-expanded state have a plurality of folds that each define a two-sided section of a triangle.

10. The spinal implant of claim 1, wherein the plurality of folds are formed from adjacent segments.

11. The spinal implant of claim 1, wherein the superior sidewall includes at least three two-sided sections of a triangle formed therein.

12. The spinal implant of claim 11, wherein the triangles are formed from at least six segments angled with respect to one another.

13. The spinal implant of claim 1, wherein the inferior sidewall includes at least three two-sided sections of a triangle formed therein.

14. The spinal implant of claim 13, wherein the triangles are formed from at least six segments angled with respect to one another.

15. The spinal implant of claim 1, wherein a base of each triangle is oriented towards a center of the implant.

* * * * *